United States Patent [19]

Christensen, IV et al.

[11] Patent Number: 5,449,687
[45] Date of Patent: Sep. 12, 1995

[54] 4-PHENYL-1,2-CYCLOHEXYL DERIVATIVES AND ANTI-INFLAMMATORY COMPOSITIONS AND METHODS THEREOF

[75] Inventors: Siegfried B. Christensen, IV, Philadelphia, Pa.; Paul E. Bender, Cherry Hill, N.J.; Cornelia J. Forster, Bensalem, Pa.; John G. Gleason, Downingtown, Pa.

[73] Assignee: SmithKline Beecham Corporation, Philadelphia, Pa.

[21] Appl. No.: 313,097

[22] Filed: Sep. 29, 1994

Related U.S. Application Data

[63] Continuation-in-part of Ser. No. 968,806, Oct. 30, 1992, abandoned, which is a continuation-in-part of Ser. No. 862,114, Apr. 2, 1992, abandoned.

[51] Int. Cl.$^6$ .................. A61K 31/275; C07C 255/46
[52] U.S. Cl. .................. 514/520; 514/521; 558/426
[58] Field of Search ............. 514/520, 521, 886; 558/426

[56] References Cited

U.S. PATENT DOCUMENTS 4,795,757  1/1989  Regan et al. .................. 514/415

OTHER PUBLICATIONS

Chemical Abstracts, vol. 113, No. 1, Abstract 5823s, 1990.

Primary Examiner—Jacqueline Haley
Attorney, Agent, or Firm—James M. Kanagy; Stuart R. Suter; Edward T. Lentz

[57] ABSTRACT

Novel compounds of Formulas (I) and (II)

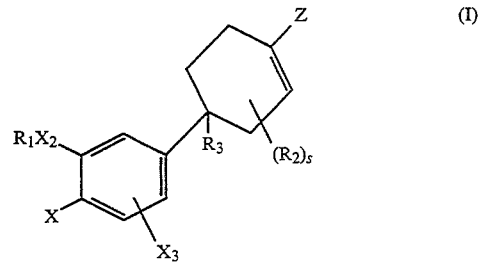

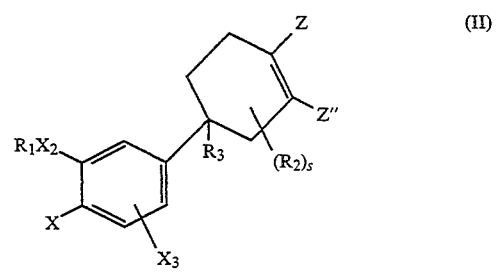

are described herein. These compounds inhibit the production of Tumor Necrosis Factor and are useful in the treatment of disease states mediated or exacerbated by TNF production; these compounds are also useful in the mediation or inhibition of enzymatic or catalytic activity of phosphodiesterase IV.

6 Claims, No Drawings

4-PHENYL-1,2-CYCLOHEXYL DERIVATIVES AND ANTI-INFLAMMATORY COMPOSITIONS AND METHODS THEREOF

This application is a National Stage application of PCT/US93/02230 filed Mar. 12, 1993, now WO 93/19720, published Oct. 14, 1993, which is a continuation-in-part of PCT/US93/02046, filed Mar. 5, 1993, now abandoned, which is a continuation-in-part of U.S. application 07/862,114, filed Apr. 2, 1992, now abandoned.

FIELD OF THE INVENTION

The present invention relates to novel compounds, pharmaceutical compositions containing these compounds, and their use in treating allergic and inflammatory diseases and for inhibiting the production of Tumor Necrosis Factor (TNF).

BACKGROUND OF THE INVENTION

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3', 5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2-}$ ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase shotfid be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Antiasthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (TNF), a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, eachexit secondary to human acquired immune deficiency syndrome (AIDS), AIDS, ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportuni stic infections and/or unusual neoplasm s. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for vital replication and the level of vital replication is dependent upon the activation state of the cells. [See Rosenberg et al., The Immunopathogenesis of HIV Infection, Advances in Immunology, Vol. 57, 1989]. Monokines, such as TNF, have been shown to activate HIV replication in monocytes and/or macrophages [See Poli et al., Proc. Natl. Acad. Sci., 87:782–784, 1990], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically Candida albicans has been shown to induce TNF production in vitro in human monocytes and natural killer cells. [See Riipi et al., Infection and Immunity, 58(9):2750–54, 1990; and Jafari et al., Journal of Infectious Diseases, 164:389–95, 1991. See also Wasan et al., Antimicrobial Agents and Chemotherapy, 35,(10):2046–48, 1991; and Luke et al., Journal of Infectious Diseases, 162:211–214,1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

This invention relates to the novel compounds of Formulas (I) and (II) as shown below, useful in the mediation or inhibition of the enzymatic activity (or catalytic activity) of phosphodiesterase IV (PDE IV). These compounds also have Tumor Necrosis Factor (TNF) inhibitory activity.

This invention also relates to the pharmaceutical compositions comprising a compound of Formulas (I) or (II) and a pharmaceutically acceptable carrier or diluent.

The invention also relates to a method of mediation or inhibition of the enzymatic activity (or catalytic activity) of PDE IV in mammals, including humans, which comprises administering to a mammal in need thereof an effective amount of a compound of Formula (I) or (II) as shown below.

The invention further provides a method for the treatment of allergic and inflammatory disease which comprises administering to a mammal, including humans, in need thereof, an effective amount of a compound of Formula (I) or (II).

The invention also provides a method for the treatment of asthma which comprises administering to a mammal, including humans, in need thereof, an effective amount of a compound of Formula (I) or (II).

This invention also relates to a method of inhibiting TNF production in a mammal, including humans, which method comprises administering to a mammal in need of such treatment, an effective TNF inhibiting amount of a compound of Formula (I) or (if). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (I) or (II).

Compounds of Formula (I) or (II) are also useful in the treatment of additional viral infections, where such viruses are sensitive to upregulation by TNF or will elicit TNF production in vivo.

In addition, compounds of Formula (I) or (II) are also useful in treating yeast and fungal infections, where such yeast and fungi are sensitive to upregulation by TNF or will elicit TNF production in vivo.

The compounds of Formula (I) are represented by the following structure:

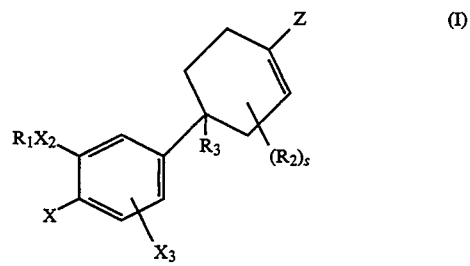

wherein: $R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties may be optionally substituted with one or more halogens;

m is 0 to 2;
n is 1 to 4;
r is 1 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy $C_{1-3}$ alkyl, halo substituted aryloxy $C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in $-(CR_4R_5)_nO(CR_4R_5)_mR_6$;

X is $YR_2$, halogen, nitro, $NR_4R_5$, or formyl amine;
Y is O or $S(O)m'$;
m' is 0, 1, or 2;
$X_2$ is O or $NR_8$;
$X_3$ is hydrogen or X;
$R_2$ is independently selected from $-CH_3$ or $-CH_2CH_3$ optionlly substituted by 1 or more halogens; is 0 to 4;

$R_3$ is hydrogen, halogen, $C_{1-4}$ alkyl, $CH_2NHC(O)C(O)NH_2$, halo-substituted $C_{1-4}$ alkyl, $-CH=CR_8'R_8'$, cyclopropyl optionally substituted by $R_8'$, CN, $OR_8$, $CH_2OR_8$, $NR_8R_{10}$, $CH_2NR_8R_{10}$, $C(Z')H$, $C(O)OR_8$, $C(O)NR_8R_{10}$, or $C\equiv CR_8'$;

Z' is $S(O)_{m'}R_9$, $OS(O)_2R_9$, $OR_9$, $OC(O)NR_8R_9$, $OC(O)(O)_qR_7$, $O(CR_4R_5)_nOR_9$, or $NR_9R_9$;

Z' is O, $NR_8$, $NNR_8R_8$, $NOR_8$, NCN, $C(-CN)_2$, $CR_8CN$, $CR_8NO_2$, $CR_8C(O)OR_8$, $CR_8C(O)NR_8R_8$, $C(-CN)NO_2$, $C(-CN)C(O)OR_9$, or $C(-CN)C(O)NR_8R_8$;

q is 0 or 1;

$R_7$ is independently hydrogen or $R_9$;

$R_8$ is independently selected from hydrogen or $C_{1-4}$ alkyl optionally substituted by one to three fluorines, or when $R_8$ and $R_{10}$ are as $-NR_8R_{10}$ they may together with the nitrogen form a 5 to 7 membered ring optionally containing one or more additional heteroatom selected from O, N, or S;

$R_8'$ is $R_8$ or fluorine;

$R_9$ is independently $C_{1-10}$alkyl, $C_{2-10}$alkenyl, $C_{3-7}$cycloalkyl, $C_{4-6}$ cycloalkenyl, aryl, arylalkyl, heteroaryl, heteroarylalkyl, each of which may be optionally substituted by one or more fluorine atoms, or two $R_9$ terms appearing as $NR_9R_9$ may together with the nitrogen form a 5 to 7 membered ring optionally containing one or more additional heteroatoms selected from O, N, or S;

$R_{10}$ is $OR_8$ or $R_8$;

provided that:

f) when q is 1 in $OC(O)(O)_qR_7$, then $R_7$ is not hydrogen;

g) when Z' is $NR_8$, then $R_8$ is not hydrogen; or the pharmaceutically acceptable salts thereof.

The other set of compounds of this invention are represented by Formula (II):

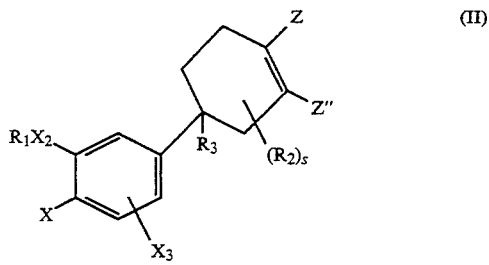

wherein the several groups are the same as those of Formula (I) and:

Z is also $NHR_{14}$;

Z" is $C(Y')R_{14}$, $C(O)OR_{14}$, $C(Y')NR_{10}R_{14}$, $C(NR_{10})NR_{10}R_{14}$, CN, $C(NOR_8)R_{14}$, $C(NOR_{14})R_8$, $C(NR_8)NR_{10}R_{14}$, $C(NR_{14})NR_8R_8$ $C(NCN)NR_{10}$ $R_{14}$, $C(NCN)SR_{11}$, (2-, 4- or 5-imidazolyl), (3-, 4- or 5-pyrazolyl), (4- or 5-triazolyl [1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxa-zolidinyl), (2-, 4-, or 5-thiazolidinyl), or (2-, 4-, or 5-imidazolidinyl); wherein all of the heterocylic ting systems may be optionally substituted one or more times by $R_{14}$;

Y' is O or S;

$R_{11}$ is $C_{1-4}$ alkyl optionally substituted by one to three fluorines;

$R_{12}$ is $C_{3-7}$ cycloalkyl, (2-, 3- or 4-pyridyl), pyrimidyl, pyrazolyl, (1- or 2-imidazolyl), thiazolyl, triazolyl, pyrrolyl, piperazinyl, piperidinyl, morpholinyl, furanyl, (2- or 3-thienyl), (4- or 5-thiazolyl), quinolinyl, naphthyl, or phenyl;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstimted or substituted by one or two $C_{1-2}$ alkyl groups;

$R_{14}$ is hydrogen or $R_{15}$; or when $R_{10}$ and $R_{14}$ are as $NR_{10}R_{14}$ they may together with the nitrogen form a 5 to 7 membered ring optionally containing one or more additional heteroatoms selected from O/N/or S;

$R_{15}$ is $-(CR_4R_5)_rR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, -F, -Br, -Cl, -NO$_2$, -Si(R$_4$)$_2$, -NR$_8$R$_{10}$, -C(O)R$_8$, -C(O)OR, $_{-OR8}$, -CN, -C(O)NR$_8$R$_{10}$, -OC(O)NR$_8$R$_{10}$, -OC(O)R$_8$, -NR$_{10}$C(O)NR$_8$R$_{10}$, -NR$_{10}$C(O)RS, -NR$_{10}$C(O)OR$_9$, -NR$_{10}$C(O)R$_{13}$, -C(NR$_{10}$)NR$_8$R$_{10}$, -C(NCN)NR$_8$R$_{10}$, -C(NCN)SR$_{11}$, -NR$_{10}$C(NCN)SR$_{11}$, -NR$_{10}$C(NCN)NR$_{10}$R$_8$, -NR$_{10}$S(O)$_2$R$_9$, -S(O)$_m$'R$_{11}$, -NR$_{10}$C(O)C(O)NR$_8$R$_{10}$, -NR$_{10}$C(O)C(O)R$_{10}$, thiazolyl, imidazolyl, oxazolyl, pyrazolyl, triazolyl, or tetrazolyl;

r is 0, 1, or 2;

provided that:

h) when $R_{12}$ is N-pyrazolyl, N-imidazolyl, N-triazolyl, N-pyrrolyl, N-piperazinyl, Npiperidinyl, or N-morpholinyl, then q is not 1;

or the pharmaceutically acceptable salts thereof.

DETAILED DESCRIPTION OF THE INVENTION

This invention also relates to a method of mediating or inhibiting the enzymatic activity (or catalytic activity) of PDE IV in a mammal in need thereof and to inhibiting the production of TNF in a mammal in need thereof, which comprises administering to said mammal an effective amount of a compound of Formula (I) or (ID).

Phosphodiesterase IV inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and central nervous system disorders such as depression and multi-infarct dementia.

The viruses contemplated for treatment herein are those that produce TNF as a result of infection, or those which are sensitive to inhibition, such as by decreased replication, directly or indirectly, by the TNF inhibitors of Formula (I) or (II). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (I) or (II).

The compounds of this invention may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, capfine arthritis virus, visna virus, maedi virus and other lentiviruses.

The compounds of this invention are also useful in treating yeast and fungal infections, where such yeast and fungi are sensitive to upregulation by TNF or will elicit TNF production in vivo. A preferred disease state for treatment is fungal meningitis. Additionally, the compounds of Formula (I) or (II) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazole; the class of compounds called the triazoles, such as fluconazole, and itranazole, and the class of compound called the Amphotericins, in particular Amphotericin B and liposomal Amphotericin B.

The compounds of Formula (I) or (II) may also be used for inhibiting and/or reducing the toxicity of an anti-fungal, anti-bacterial or anti-vital agent by administering an effective amount of a compound of Formula (I) or (II) to a mammal in need of such treatment. Preferably, a compound of Formula (I) or (II) is administered for inhibiting or reducing the toxicity of the Amphoteficin class of compounds, in particular Amphoteficin B.

Preferred compounds are as follows:

When $R_1$ for the compounds of the Formula (I) is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties $-CF_3$, $-CH_2F$, $-CHF_2$, $-CF_2CHF_2$, $-CH_2CF_3$, and $-CH_2CHF_2$. Preferred $R_1$ substitutents for the compounds of the Formula (I) are $CH_2$-cyclopropyl, $CH_2$-$C_{5-6}$ cycloalkyl, $C_{4-6}$ cycloalkyl, $C_{7-11}$ polycycloalkyl, (3- or 4-cyclopentenyl), phenyl, tetrahydrofuran-3-yl, benzyl or $C_{1-2}$ alkyl optionally substituted by 1 or more fluorines', $-(CH_2)_{1-3}C(O)O(CH_2)_{0-2}CH_3$, $-(CH_2)_{1-3}O(CH_2)_{0-2}CH_3$, an $-(CH_2)_{2-4}OH$.

When the $R_1$ term contains the moiety $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be $-CH_2CH(-CH_3)-$, for instance. The individual hydrogen atoms of the repeating methylene unit or the branching hydrocarbon can optionally be substituted by fluorine independent of each other to yield, for instance, the preferred $R_1$ substitutions, as noted above.

When $R_1$ is a $C_{7-11}$ polycycloalkyl, examples are bicyclo[2.2.1]-heptyl, bicyclo[2.2.2]octyl, bicyclo[3.2.1]octyl, tricyclo[5.2.1.0$^{2,6}$]decyl, etc. additional examples of which are described in Saccamano et al., WO 87/06576, published Nov. 5, 1987, whose disclosure is incorporated herein by reference in its entirety.

Z is $S(O)_m'R_9$, $OS(O)_2R_9$, $OR_9$, $OC(O)NR_7R_9$, $OC(O)(O)_qR_7$, $O(CR_4R_5)_nOR_9$, or $NR_9R_9$ in compounds of the Formula (I) and also $NHR_{14}$ in compounds of the Formula (II). Preferably, q is 0. Preferred Z terms are $S(O)_m'R_9$, $OS(O)_2R_9$, $OR_9$, $OC(O)NR_7R_9$, $O(CR_4R_5)_nOR_9$, or $NR_9R_9$ in compounds of the Formula (I) and also $NHR_{14}$ in compounds of the Formula (II).

Z" in Formula (II) is preferably $C(O)R_{14}$, $C(O)OR_{14}$, $C(O)NR_{10}R_{14}$, $C(NR_{10})NR_{10}R_{14}$, CN, $C(NOR_8)R_{14}$, $C(NR_8)NR_{10}R_{14}$, $C(NCN)NR_8R_{14}$, $C(NCN)SR_{11}$, (1-, 4- or 5-{$R_{14}$}-2-imidazolyl), (1-, 4- or 5-{$R_{14}$}-3-pyrazolyl),(1-, 2- or 5-{$R_{14}$}-4-triazolyl[1,2,31), (1-, 2-, 4- or 5-{$R_{14}$}-3-triazolyl[1,2,4]), (1- or 2-{$R_{14}$}-5-tetrazolyl), (4- or 5-{$R_{14}$}-2-oxazolyl), (3- or 4-{$R_{14}$}-5-isoxazolyl), (3-{$R_{14}$}-5-oxadiazolyl[1,2,4]), (5-{$R_{14}$}-3-oxadiazolyl-[1,2,4),(5{$R_{14}$}-2-oxadiazolyl[1,3,4]), (5-{$R_{14}$}-2-thiadiazolyl[1,3,4]), (4- or 5-{$R_{14}$}-2-thiazolyl), (4- or 5-{$R_{14}$}-2-oxazolidinyl), (4- or 5-{$R_{14}$}-2-thiazolidinyl), ( 1-, 4- or 5-{$R_{14}$}-2-imidazolidinyl).

Preferred X groups for Formulas (I) and (II) are those wherein X is $YR_2$ and Y is oxygen. The preferred $X_2$ group Formulas (I) and (II) is that wherein $X_2$ is oxygen. The preferred $X_3$ group is hydrogen. Preferred $R_2$ groups, where applicable, are a $C_{1-2}$ alkyl optionally substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a $-CF_3$, $-CHF_2$, or $-CH_2CHF_2$ moiety. Most preferred are the $-CHF_2$ and $-CH_3$ moieties.

Preferred $R_3$ moieties are $C(O)NH_2$, $C\equiv CR_8$, CN, $C(Z')H$, $CH_2OH$, $CH_2F$, $CF_2H$, and $CF_3$. Z' is preferably O or $NOR_8$. More preferred are $C\equiv CH$ and CN.

Preferred $R_{15}$ moieties include optionally substituted-$(CH_2)_{1-2}$(cyclopropyl), $-(CH_2)_{0-2}$(cyclobutyl),-$(CH_2)_{0-2}$(cyclopentyl),-$(CH_2)_{0-2}$(cyclohexyl),-$(R_4R_5)_{0-2}$(2-, 3- or 4-pyridyl), $(R_4R_5)_{1-2}$(2-imidazolyl), $(R_4R_5)_2$(4-morpholinyl), $(R_4R_5)_2$(4-piperazinyl), $(R_4R_5)_{1-2}$(2-thienyl), $(R_4R_5)_{1-2}$(4-thiazolyl), and $(R_4R_5)_{0-2}$phenyl;

Preferred tings when the two $R_9$ terms in the moiety $NR_9R_9$ together with the nitrogen to which they are attached form a a 5 to 7 membered ring optionally containing at least one additional heteroatom selected from O, N or S include, but are not limited to, the morpholinyl, piperazinyl, or pyrrolyl rings.

Preferred rings when $R_8$ and $R_{10}$ in the moiety -$NR_8R_{10}$ together with the nitrogen to which they are attached form a a 5 to 7 membered ting optionally containing at least one additional heteroatom selected from O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-tetrazolyl, 2-tetrazloyl, morpholinyl, piperazinyl, 4-($R_8$)-1-piperazinyl, or pyrrolyl ring.

Preferred rings when $R_{10}$ and $R_{14}$ in the moiety -$NR_{10}R_{14}$ together with the nitrogen to which they are attached may form a 5 to 7 membered ting optionally containing at least one additional heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective tings may be additionally substituted, where applicable, on an available nitrogen or carbon by the moiety $R_{15}$ as described herein for Formula (II). IHustrations of such carbon substitutions includes, but is not limited to, 2-($R_{15}$)-1-imidazolyl, 4-($R_{15}$)-1-imidazolyl, 5-($R_{15}$)-1 -imidazolyl, 3-($R_{15}$)- 1-pyrazolyl, 4-($R_{15}$)-1-pyrazolyl, 5-($R_{15}$)-1-pyrazolyl, 4-($R_{15}$)-2-triazolyl, 5-($R_{15}$)-2-triazolyl, 4-($R_{15}$)-1-triazolyl, 5-($R_{15}$)-1-triazolyl, 5-($R_{15}$)-1-tetrazolyl, and 5-($R_{15}$)-2-tetrazolyl. Applicable nitrogen substitution by $R_{15}$ includes, but is not limited to, 1-($R_{15}$)-2-tetrazolyl, 2-($R_{15}$)-1-tetrazolyl, 4-($R_{15}$)-1-piperazinyl. Where applicable, the ring may be substituted one or more times by $R_{15}$.

Preferred groups for -NR$_{10}$R$_{14}$ which contain a heterocyclic ring are 5-(R$_{14}$)-1-tetrazolyl, 2-(R$_{14}$)-1-imidazolyl, 5-(R$_{14}$)-2-tetrazolyl, 4-(R$_{14}$)-1-piperazinyl, or 4-(R$_{15}$)-1-piperazinyl.

Preferred rings for R$_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-isoxazolyl),(3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4- or 5-thiazolidinyl), or 5-imidazolidinyl).

When the R$_{15}$ group is optionally substituted by a heterocyclic ring such as imidazolyl, pyrazolyl, triazolyl, tetrazolyl, or thiazolyl, the heterocyclic ring itself may be optionally substituted by R$_8$ either on an available nitrogen or carbon atom, such as 1-(R$_8$)-2-imidazolyl, 1-(R$_8$)-4-imidazolyl, 1-(R$_8$)-5-imidazolyl, 1-(R$_8$)-3-pyrazolyl, 1-(R$_8$)-4-pyrazolyl, 1-(R$_8$)-5-pyrazolyl, 1-(R$_8$)-4-triazolyl, or 1-(R$_8$)-5-triazolyl. Where applicable, the ring may be substituted one or more times by R$_8$.

Preferred are those compounds of Formulas (I) and (II) wherein R$_1$ is -CH$_2$-cyclopropyl, -CH$_2$-C$_{5-6}$ cycloalkyl, -C$_{4-6}$ cycloalkyl, tetrahydrofuran-3-yl, (3- or 4-cyclopentenyl), benzyl or -C$_{1-2}$ alkyl optionally substituted by 1 or more fluorines, and -(CH$_2$)2-4 OH; R$_2$ is methyl or fluoro-substituted alkyl, R$_3$ is CN or C≡CR$_8$; and X is YR$_2$.

Most preferred are those compounds wherein R$_1$ is -CH$_2$-cyclopropyl, cyclopentyl, methyl or CF$_2$H; R$_3$ is CN or C≡CH; X is YR$_2$; Y is oxygen; X$_2$ is oxygen; X$_3$ is hydrogen; and R$_2$ is CF$_2$H or methyl.

A preferred subgenus of the compounds of the Formula (I) is the compounds of the Formula (Ia)

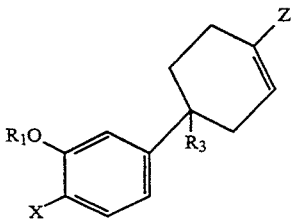
(Ia)

wherein:

R$_1$ is CH$_2$-cyclopropyl, CH$_2$-C$_{5-6}$ cycloalkyl, C$_{4-6}$ cycloalkyl, C$_{7-11}$ polycycloalkyl, (3-or 4-cyclopentenyl), phenyl, tetrahydrofuran-3-yl, benzyl or C$_{1-2}$ alkyl optionally substituted by 1 or more fluorines, -(CH$_2$)$_{1-3}$C(O)O(CH$_2$)$_{0-2}$CH$_3$, -(CH$_2$)$_{1-3}$O(CH$_2$)$_{0-2}$CH$_3$, and -(CH$_2$)$_{2-4}$OH;

X is YR$_2$, halogen, nitro, NR$_4$R$_5$, or formyl amine;

Y is O or S(O)m′;

m′ is 0, 1, or 2;

R$_2$ is -CH$_3$ or -CH$_2$CH$_3$ optionally substituted by 1 or more halogens;

R$_3$ is hydrogen, C$_{1-4}$ alkyl, CH$_2$NHC(O)C(O)NH$_2$, halo-substituted C$_{1-4}$ alkyl, CN, CH$_2$OR$_8$, C(Z′)H, C(O)OR$_8$, C(O)NR$_8$R$_{10}$, or C≡CR$_8$;

Z is S(O)$_{m'}$R$_9$, OS(O)$_2$R$_9$, OR$_9$, OC(O)NR$_7$R$_9$, OC(O)(O)$_q$R$_7$, O(CR$_4$R$_5$)$_n$OR$_9$, or NR$_9$R$_9$;

Z′ is O or NOR$_8$;

q is 0 or 1;

R$_7$ is independently hydrogen or R$_9$;

R$_8$ is independently selected from hydrogen or C$_{1-4}$ alkyl optionally substituted by one to three fluorines;

R$_{8'}$ is R$_8$ or fluorine;

R$_9$ is independently C$_{1-10}$ alkyl, C$_{2-10}$ alkenyl, C$_{3-7}$ cycloalkyl, C$_{4-6}$ cycloalkenyl, aryl, arylalkyl, heteroaryl, heteroarylalkyl, each of which may be optionally substituted by one or more fluorine atoms, or two R$_9$ terms appearing as NR$_9$R$_9$ may together with the nitrogen form a 5 to 7 membered ring optionally containing one or more additional heteroatoms selected from O/N-/or S;

R$_{10}$ is -OR$_8$ or R$_8$;

provided that:

f) when q is 1 in OC(O)(O)$_q$R$_7$, then R$_7$ is not hydrogen;

g) when Z′ is NR$_8$ then R$_8$ is not hydrogen;

or the pharmaceutically acceptable salts thereof.

Exemplified compounds of Formula (I) are:

4-cyano-4-(3-cyclopentyloxy-4-methoxyphenyl)cyclohex-1-en-1-yl trifluoromethylsulfonate;

4-cyano-4-(3-cyclopentyloxy-4-methoxyphenyl)-1-methoxycyclohex-1-ene; and 4-cyano-4-(3-cyclopropylmethoxy-4-methoxyphenyl)cyclohex-1-en-1-yl trifluoromethylsulfonate.

Exemplified compounds of Formula (II) are:

2-carbomethoxy-4-cyano-4-(3-cyclopropylmethoxy-4-methoxyphenyl)-1-(methoxymethyloxy)cyclohex-1-ene;

2-carboxy-4-cyano-4-(3-cyclopropylmethoxy-4-methoxyphenyl) -1-(methoxymethyloxy)cyclohex-1-ene;

2-aminocarbonyl-4-cyano-4-(3-cyclopropylmethoxy-4-methoxyphenyl)-1-(methoxymethyloxy)cyclohex-1-ene;

1-amino-4-(3-cyclopropylmethoxy-4-difluoromethoxyphenyl])-2,4-dicyanocyclohex-1-ene;

2-carbomethoxy-4-cyano-4-(3-cyclopropylmethoxy-4-difluoromethoxyphenyl) -1-(methoxymethyloxy)cyclohex-1-ene;

2-carboxy-4-cyano-4-(3-cyclopropylmethoxy-4-difluoromethoxyphenyl) -1-(methoxymethyloxy)cyclohex-1-ene;

2-aminocarbonyl-4-cyano-4-(3-cyclopropylmethoxy-4-difluoromethoxyphenyl) -1-(methoxymethyloxy)cyclohex-1-ene;

1-amino-2-carbomethoxy-4-cyano-4-(3-cyclopentyloxy-4-methoxyphenyl)cyclohex-1-ene;

methyl 2-[S-(α)-p-bromophenethylamino]-5-cyano-5-(R and S)-(3-cyclopentyloxy-4-difluoromethoxyphenyl) cyclohex-1-en-1-yl carboxylate;

methyl 2-amino-5-cyano-5-(3-cyclopropylmethoxy-4-difluoromethoxyphenyl)-cyclohex -1-en-1-yl carboxylate;

methyl 2-benzylamino-5-cyano-5-(3-cyclopropylmethoxy-4-methoxyphenyl)cyclohex-1-en-1-yl carboxylate; and methyl 2-[S-(α)-p-nitrophenethylamino]-5-cyano-5-(R and S)-(3-cyclopentyloxy-4-difluoromethoxyphenyl) cyclohex-1-en-1-yl carboxylate.

It will be recognized that some of the compounds of Formula (I) and (II) may exist in both racemic and optically active forms; some may also exist in distinct diastereomefic forms possessing distinct physical and biological properties. All of these compounds are considered to be within the scope of the present invention.

Compounds of Formula (II) may exist in a tautomeric form, such as the imine form. This may be represented by the =Z (or ylidine bond) being exocyclic to the cyclohexane ring

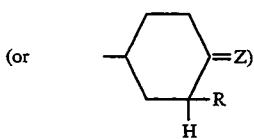

as contrasted to the endocyclic or -C(-ZH)=C(-R)- moiety wherein the cyclohexane ring is now unsaturated in the 1-2 position, i.e. cyclohex-1-ene, or

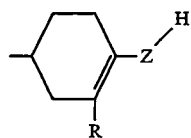

and R is Z" in Formula (II). It is also recognized that the 2-position of the ring in the exocyclic form can be substituted (R) such as in the compounds of Formula (H).

The term "$C_{1-3}$ alkyl", "$C_{1-4}$ alkyl", "$C_{1-6}$ alkyl" or "alkyl" groups includes both straight or branched chain radicals of 1 to 10, unless the chain length is limited thereto, including, but not limited to methyl, ethyl, n-propyl, isopropyl, n-butyl, sec-butyl, isobutyl, tert-butyl, and the like.

"Alkenyl" means both straight or branched chain radicals of 1 to 6 carbon lengths, unless the chain length is limited thereto, including but not limited to vinyl, 1-propenyl, 2-propenyl, 2-propynyl, or 3-methyl-2-propenyl.

The term "cycloalkyl" or "cycloalkyl alkyl" means groups of 3–7 carbon atoms, such as cyclopropyl, cyclopropylmethyl, cyclopentyl, or cyclohexyl.

"Aryl" or "aralkyl", unless specified otherwise, means an aromatic ring or ring system of 6–10 carbon atoms, such as phenyl, benzyl, phenethyl, or naphthyl. Preferably the aryl is monocyclic, i.e, phenyl. The alkyl chain is meant to include both straight or branched chain radicals of 1 to 4 carbon atoms.

"Heteroaryl" means an aromatic ring system containing one or more heteroatoms, such as imidazolyl, triazolyl, oxazolyl, pyfidyl, pyrimidyl, pyrazolyl, pyrrolyl, furanyl, or thienyl.

"Halo" means all halogens, i.e., chloro, fiuoro, bromo, or iodo.

Inhibiting the production of IL-1" or "inhibiting the production of TNF" means:

a) a decrease of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postranslational event.

The phrase "TNF mediated disease or disease states" means any and all disease states in which TNF plays a role, either by production of TNF itself, or by TNF causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF. As TNF-$\beta$ (also known as lymphotoxin) has close structural homology with TNF-$\alpha$ (also known as cachectin), and since each induces similar biologic responses and binds to the same cellular receptor, both TNF-$\alpha$ and TNF-$\beta$ are inhibited by the compounds of the present invention and thus are herein referred to collectively as "TNF" unless specifically delineated otherwise. Preferably TNF-$\alpha$ is inhibited.

"Cytokine" means any secreted polypepticle that affects the functions of cells, and is a molecule which modulates interactions between cells in immune, inflammatory, or hematopoietic responses. A cytokine includes, but is not limited to, monokines and lymphokines regardless of which cells produce them.

The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferably, his cytokine is TNF-$\alpha$.

All of the compounds of Formulas (I) and (II) are useful in the method of inhibiting the production of TNF, preferably by macrophages, monocytes or macrophages and monocytes, in a mammal, including humans, in need thereof. All of the compounds of Formulas (I) and (II) are useful in the method of inhibiting or mediating the enzymatic or catalytic activity of PDE IV and in treatment of disease states mediated thereby.

METHODS OF PREPARATION:

Preparation of the compounds of the Formula (I) can be carried out by one of skill in the an according to the procedures outlined in the Examples, infra. The preparation of any remaining compounds of the Formula (I) not described therein may be prepared by the analogous processes disclosed herein which comprise:

a) reacting a compound of the Formula (2)

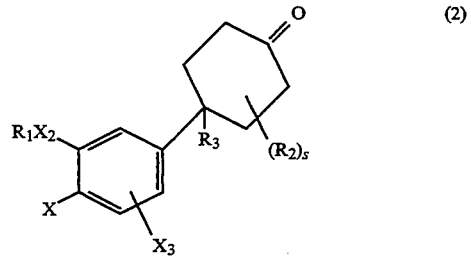

wherein $R_1$ represents $R_1$ as defined in relation to Formula (I) or a group convertable to $R_1$ and X, $X_2$ and $X_3$ represent X, $X_2$ and $X_3$ as defined in relation to Formula (I) or a group convertable to X, $X_2$ or $X_3$ and $R_2$ and $R_3$ represent $R_2$ and $R_3$ as defined in relation to Formula (I) or a group convertable to $R_2$ or $R_3$, with a suitable base in a suitable non-reacting solvent followed by reaction with a suitable alkylating or acylating agent [$LS(O)_2R_9$, $LR_9$, $L(CR_4R_5)_nOR_9$, $LC(O)(O)_qR_7$, or $LC(O)NR_7R_9$, wherein L is a leaving group] to provide compounds of the Formula (I) wherein Z is $OS(O)_2R_9$, $OR_9$, $O(CR_4R_5)_nOR_9$, $OC(O)(O)_qR_7$, or $OC(O)NR_7R_7$ and $R_3$ is other than C(=Z')H; preparation of such compounds of Formula (I) wherein $R_3$ is C(=Z')H proceeds in an analogous fashion from the compound of Formula (2) wherein =Z' is an aldehyde protecting group, such as a dimethylacetal or a dioxolane, followed by deprotection to the aldehyde and subsequent elaboration by standard procedures known to those of skill in the art to the remaining compounds of Formula (I) wherein Z' is other than 0.

b) preparation of compounds of the Formula (I) wherein Z is $NR_9R_9$ or $SR_9$ proceeds by reacting a compound of the Formula (2) with an appropriate amine of the formula $HNR_9R_9$ or an appropriate thiol of the formula $HSR_9$ in the presence of a suitable acidic or basic catalyst with scavenging or removal of water. Alternatively, such compounds may be obtained by treatment of an appropriate compound of the Formula (I) wherein Z is $OS(O)_2R_9$, $OR_9$, or $O(CR_4R_5)_nOR_9$ and $R_3$ is other than C(=Z')H with an appropriate amine of the formula $HNR_9R_9$ or an appropriate thiol of the formula $HSR_9$ in an aprotic solvent; preparation of such compounds of Formula (I) wherein $R_3$ is C(=Z')H proceeds in an analogous fashion from the compound of Formula (2) wherein =Z' is an aldehyde protecting group, such as a dimethylacetal or a dioxolane, followed by deprotection to the aldehyde and subsequent elaboration by standard procedures known to those of skill in the art to the remaining compounds of Formula (I) wherein Z' is other than 0.

Compounds of the Formula (2) may be prepared in time by the processes described in co-pending U.S. application Ser. No. 07/862,083 filed Apr. 2, 1992 and its corresponding continuation-in-part application U.S. Ser. No. 968,753 filed Oct. 30, 1992.

Some compounds of the Formula (II) may be prepared by processes analogous to those above by reacting the appropriate reagent with a compound of the Formula (3)

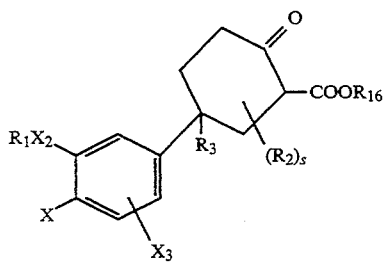

(3)

wherein $R_1$ represents $R_1$ as defined in relation to Formula (I) or a group convertable to $R_1$ and X, $X_2$ and $X_3$ represent X, $X_2$ and $X_3$ as defined in relation to Formula (I) or a group convertable to X, $X_2$ or $X_3$ and $R_3$ represents $R_3$ as defined in relation to Formula (I) or a group convertable to $R_3$ and $R_{16}$ is an alkyl, phenyl or benzyl group.

Compounds of the Formula (3) may be prepared in turn by the processes described in co-pending U.S. application Ser. No. 07/862,083 filed Apr. 2, 1992 and its corresponding continuation-in-part filed on even date herewith.

In addition, some compounds of the Formula (II) may be prepared by reacting a compound of the Formula (4)

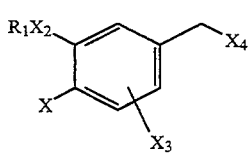

(4)

$R_1$ represents $R_1$ as defined in relation to Formula (I) or a group convertable to $R_1$ and X, $X_2$ and $X_3$ represent X, $X_2$ and $X_3$ as defined in relation to Formula (I) or a group convertable to X, $X_2$ or $X_3$ and $R_3$ represents $R_3$ as defined in relation to Formula (I) or a group convertable to $R_3$, and $X_4$ is CN with an excess of acrylonitrile in the presence of a base, such as excess metal hydride, or catalytic or excess quaternary amine base, such as benzyltrimethylammonium hydroxide, in a suitable non-reacting solvent, such as tetrahydrofuran or 1,2-dimethoxyethane when a metal hydride base is used or these solvents or acetonitrile when a quaternary amine base is used, to provide a compound of the Formula (5)

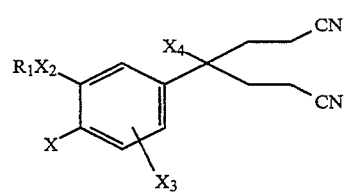

(5)

wherein $X_4$ is CN; reaction of a compound of the Formula (5) with a base, such as excess metal hydride, in a suitable non-reacting solvent, such as tetrahydrofuran or 1,2-dimethoxyethane, at an elevated temperature then provides a compound of the Formula (6)

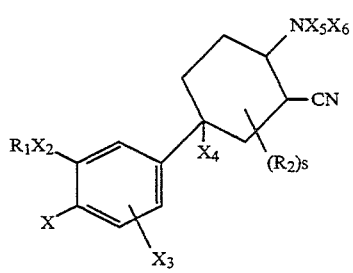

(6)

wherein $X_4$ is CN and $X_5$ and $X_6$ are both H; alternatively, a compound of the Formula (6) [a subset of the compounds of the Formula (II)] may be obtained directly from a compound of Formula (5) wherein $X_4$ is as described above by reaction with an excess of optionally $R_2$-substituted acrylonitrile, with excess base, such as a metal hydride, in a suitable non-reacting solvent, such as tetrahydrofuran or 1,2-dimethoxyethane, at an elevated temperature.

Treatment of a compound of the Formula (6) with an acid, e.g., 6N hydrochloric acid at ambient or elevated temperature, in a solvent, such as ethanol, with or without a co-solvent, such as chloroform, provides a compound of Formula (7), which may be converted to compounds of Formula (II) by processes analogous to those described above.

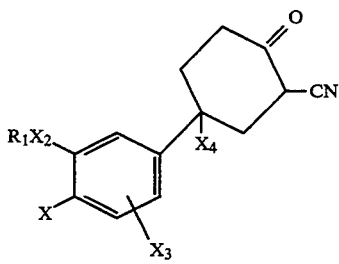

Compounds of Formula (8)

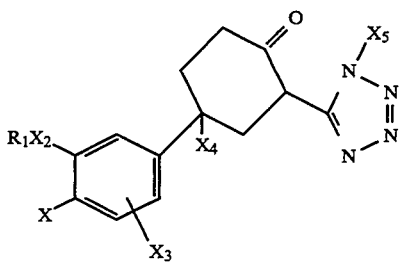

wherein $X_5$ is H, are prepared by heating compounds of the Formula (7) in a soludon of hydrazoic acid generated in situ by, e.g., admixture of an alkalai metal azide, such as sodium azide, with an ammonium halide, such as triethylamino hydrochloride, in a polar non-protic solvent such as N-methylpyrrolidinone such compounds may be converted to compound of Formula (II) by processes analogous to those described above.

Some compounds of Formula (II) may be prepared from other compounds of the Formula (II) by, e.g., functional group manipulation of the Z" group either preceeding functional group manipulation of the Z group or, in some cases, with appropriate protection and aleprotection of chemically sensitive Z group functionality during functional group manipulation of the Z" group. Some such manipulations of the Z" group may be accomplished by the processes described in co-pending U.S. application Ser. No. 862,030 filed Apr. 2, 1992 and its corresponding continuation-in-part application U.S. Ser. No. 968,762 filed Oct. 30, 1992.

The following examples are set out to illustrate how to make the compounds of this invention and methods for determining associated therapeutic activity. These examples are not intended to limit the invention in any manner, their purpose is illustrative rather than limiting.

SYNTHETIC, EXAMPLES

EXAMPLE 1

4-Cyano-4-(3-cyclopentyloxy-4-methoxyphenyl)-cylohex-1-en-1-yl trifluoromethylsulfonate To a solution of diisopropylamine (1.95 milliliters (hereinafter mL), 13.9 millimoles (hereinafter retool)) in tetrahydrofuran (12 mL) at 0° C. under an argon atmosphere was added n-butyllithium (5.8 mL of 2.5M solution, 14.15 retool), the resulting solution was stirred for 25 minutes (hereinafter rain) and then was cooled to −78° C. To this was added a solution of 4-cyano -4-(3-cyclopentyloxy-4-methoxyphenyl)cyclohexan-1-one (2 grams (hereinafter g), 6.64 retool) in tetrahydrofuran (9 mL). The resulting mixture was stirred at -78° C. for 2 hours (hereinafter h), at which time N-phenyl-trifluoromethylsulfonimide (4.98 g, 13.9 retool) was added. The mixture was allowed to warm slowly to room temperature and after 5h, the mixture was poured into water and extracted with methylene chloride. The organic extract was dried (potassium carbonate) and concentrated under reduced pressure. The residue was purified by flash chromatography, eluting with 4:1 hexanes/ethyl acetate, to afford an oil (1.09 g, 37%).

EXAMPLE 2

4-Cyano-4-(3-cyclopentyloxy,4-methoxyphenyl)-1-methoxycyclohex-1-ene

To a solution of 4-cyano-4-(3-cyclopentyloxy-4-methoxyphenyl)cyclohexan-1-one (0.3 g, 0.96 mmol) in dimethylformamide (3 mL) at 0° C. under an argon atmosphere was added potassium t-butoxide (0.11 g, 0.96 retool) and, 0.5h later, dimethyl sulfate (0.09 mL, 0.96 mmol). After 5 min, ammonium chloride was added, the mixture was extracted three times with ether, the organic extract was washed three times with water, once with brine, was dried (magnesium sulfate) and evaporated. Purification by flash chromatography, eluting with 9:1 hexanes/ethyl acetate, provided a white solid (0.06 g, 19%): m.p. 123°–125° C. Analysis Calc. for $C_{20}H_{25}NO_3 \cdot 0.35\ H_2O$:C 71.98, H 7.76, N 4.20; found: C 71.98, H 7.66, N 3.95

EXAMPLE 3

1-Amino-4-(3-cyclopropylmethoxy-4-difluoromethoxyphenyll)-2,4-dicyanocyclohex-1-ene 3a. 4-Cyano-4-(3-cyclopropylmethoxy-4-difluoromethoxypheny)pimelonitrile. To a stirred solution of 3-cyclopropylmethoxy-4-difluoromethoxyphenylacetonitrile (1.0 g, 3.95 mmol) in dry acetonitrile (25 mL) under an argon atmosphere was added a 40% solution of Triton-B in methanol (0.186 mL, 0.40 mmol) followed by acrylonitrile (2.9 mL, 44 retool). The solution was heated to reflux for 20 rain, quenched by addition of dilute aqueous hydrochloric acid and concentrated in vacuo. The residue was partitioned between ethyl acetate and water acidified with dilute hydrochloric acid, the organic phase was washed with brine, was dried (sodium sulfate) and the solvent was evaporated. The residue was purified by flash chromatography, eluting with 33% ethyl acetate/hexanes, and the oil was triturated with ether to provide white crystals (0.56 g, 39%): m.p. 95°–97° C.

Analysis Calc. for $C_{19}H_{19}F_2N_3O_2 \cdot \frac{1}{8}\ H_2O$: C 63.11, H5.37, N11.62; found: C 63.14, H 5.29, N 11.53.

3b. 1-Amino-4-(3-cyclopropylmethoxy-4-difluoromethoxyphenyl)-2,4-dicyanocyclohex-1-ene To a stirred suspension of sodium hydride (0.92 g, 3.07mmol) in dry 1,2-dimethoxyethane (8 mL) heated at 70° C. under an argon atmosphere was added dropwise a solution of 4-cyano-4-(3-cyclopropylmethoxy-4-difluoromethoxyphenyl)pimelonitrile (0.53 g, 1.48 mmol) in dry 1,2-dimethoxyethane (2.5 mL). After the addition, the mixture was heated to 85° C. for 20 min and then quenched into ice water. The suspension was neutralized with a few drops of acetic acid and was extracted three times with ether. The combined organic extract was washed with water, brine, was dried (sodium sulfate) and was evaporated. Half of this residue was purified by flash chromatography, eluting with 1% methanol/methylene chloride and the residue was triturated with ether to provide a tan solid (0.102 g, 38%):m.p. 147°–148.5° C. Analysis Calc. for $C_{19}H_{19}F_2N_3O_2$:C63.50, H 5.33, N 11.69; found: C 63.26, H: 5.40, N 11.40.

EXAMPLE 4

1-Amino-2- carbomethoxy-4-cyano-4-(3-cyclopropylmethoxy-4-methoxyphenyl)cyclohex-1-ene 4a. 4-Cyano-4-(3-cyclopropylmethoxy-4-methoxypheny)cyclohex-1-en-1-yl trifluoromethylsulfonate To a solution of 2,6-di-t-butyl-4-methylpyridine (0.43 g, 2.1 retool) in dichloromethane (8 mL) at room temperature under an argon atmosphere was rapidly added trifluoromethanesulfonic anhydride (0.30 mL, 1.78 mmol), followed immediately by the dropwise addition over 20 min of a solution of 2-carboxymethyl-4-cyano-4-(3-cyclopropylmethoxy -4-methoxyphenyl)cyclohexan-1-one (0.50 g, 1.4 mmol) in dichloromethane (4 mL). The mixture was stirred for 24h, was quenched with 1% hydrochloric acid, was extracted three times with dichloromethane, was dried (magnesium sulfate) and was evaporated. Purification by flash chromatography, eluting with 25% ethyl acetate/hexanes, provided a sticky white solid (0.60 g, 84 %): m.p. 73°-74° C.

4b. 1-Amino-2-carbomethoxy-4-cyano-4-(3-cyclopentyloxy-4-methoxyphenyl)-1-cyclohex -1-ene A solution of 4-cyano-4-(3-cyclopropylmethoxy-4-methoxyphenyl)-cyclohex-1-en-1-yl trifluoromethylsulfonate (0.14 g, 0.28 mmol) in N,N-dimethylformamide (2 mL) was saturated with ammonia gas and was stirred at room temperature under an argon atmosphere for 6h. The mixture was partitioned between water and ethyl acetate, the organic extract was washed three times with water, once with brine, was dried (potassium carbonate) and was evaporated. Purification by flash chromatography, eluting with 35% ethyl acetate/hexanes, followed by trimration from dichloromethane/hexanes, provided a white solid (0.074 g, 74 %): m.p. 164°-165° C.

Analysis Cate. for $C_{20}H_{24}N_2O_4 \cdot \frac{1}{2} H_2O$: C 65.74, H 6.90, N 7.67; found: C 65.72, H 6.69, N 7.58.

EXAMPLE 5

Methyl 2-[S-(α):p-bromophenethylamino]-5-cyano-5-(3-cyclopentyloxy-4-difluoromethoxyphenyl) cyclohex-1-en-1-yl carboxylate A solution of 2-carboxymethyl-4-cyano-4-(3-cyclopropylmethoxy-4-methoxyphenyl) cyclohexan-1-one (1.00 g, 2.54 mmol) and S-(α)-bromophenethylamine (1 mL) in toluene (7.5 mL) was stirred at reflux with a Dean-Stark trap for 24h and was cooled. The mixture was diluted with ether, was washed with water and brine, was dried (potassium carbonate) and was evaporated. Purification by flash chromatography, eluting with 10% ethyl acetate/hexanes, provided two separate diastereomers distinguished by their NMR spectra and TLC behavior:A:

A: a white foamy solid (0.44 g, 30%), further purified by trituration from methanol-water, to provide a white solid: m.p. 55°-58° C.; TLC Rf (20% ethyl acetate/hexanes): 0.33. Analysis Calc. for $C_{28}H_{29}BrF_2N_2O_4$: C 58.44, H 5.08 N 4.87; found: C 58.45, H 5.10, N 4.73.

B: a white solid (0.51 g, 35%), further purified by trituration from methanol-water, to provide a white solid: m.p. 55°-58° C.; TLC Rf (20% ethyl acetate/hexanes): 0.44. Analysis Calc. for $C_{28}H_{29}BrF_2N_2O_4$: C 58.44, H 5.08 N 4.87; found: C 58.32, H 5.02, N 4.75.

The following were also prepared by analogous methods:

Methyl 2-amino-5-cyano-5-(3-cyclopropylmethoxy-4-difluoromethoxyphenyl)-cyclohex -1-en-1-yl carboxylate, a solid: m.p. 149°-151° C. Analysis Calc. for $C_{20}H_{22}F_2N_2O_4 \cdot \frac{1}{4} H_2O$: C 60.52, H 5.71, N 7.14; found: C 60.50, H 5.54, N 6.85.

Methyl 2-benzylamino-5-cyano-5-(3,cyclopropylmethoxy-4-methoxyphenyl)cyclohex-1-en-1-yl carboxylate, a solid: m.p. 119°-120° C. Analysis Calc. for $C_{27}H_{30}N_2O_4 \cdot \frac{1}{4} H_2O$: C 71.90, H 6.82, N 6.21; found: C 71.80, H 6.74, N 6.24.

Methyl 2-[S-(α)-p-nitrophenethylaminol,5-cyano-5-(3-cyclopentyloxy-4-difluoromethoxyphenyl) cyclohex-1-en-1-yl carboxylate, as two separable diastereomers: A: a solid: m.p. 121°-122° C. Analysis Calc. for $C_{28}H_{29}F_2N_3O_6$: C 62.10, H 5.40, N 7.76; found: C 61.90, H 5.43, N 7.39.

B: a semi-solid.

METHODS OF TREATMENT

In order to use a compound of Formula (I) or (II) or a pharmaceutically acceptable salt thereof for the treatment of humans and other mammals, it is normally formulated in accordance with standard pharmaceutical practice as a pharmaceutical composition.

The compounds of Formula (I) or (II), or a pharmaceutically acceptable salt thereof can be used in the manufacture of a medicament for the prophylatic or therapeutic treatment of any disease state in a human or other mammal which is mediated by inhibition of PDE IV, such as but not limited to asthma, allergic, or inflammatory diseases. The compounds of Formula (I) or (II) are administered in an amount sufficient to treat such a disease in a human or other mammal.

For the purposes herein all methods of treatment and dosage regimens apply equally to both the compounds of Formula (I) or (II).

In order to use a compound of Formula (I) or (II), or a pharmaceutically acceptable salt thereof, for the treatment of humans and other mammals it is normally formulated in accordance-with standard pharmaceutical practice as a pharmaceutical composition.

The amount of a compound of Formula (I) or (II) required for therapeutic effect on topical administration will, of course, vary with the compound chosen, the nature and severity of the condition and the animal undergoing treatment, and is ultimately at the discretion of the physician.

The daily dosage regimen for oral administration is suitably about 0.001 mg/kg to 100mg/kg, preferably 0.01 mg/Kg to 40 mg/Kg, of a compound of Formula (I) or (II) or a pharmaceutically acceptable salt thereof calculated as the free acid or base, which ever is appropriate. The active ingredient may be administered from 1 to 6 times a day, sufficient to exhibit activity.

No unacceptable toxic effects are expected when these compounds are administered in accordance with the present invention.

UTILITY EXAMPLES

EXAMPLE A

Inhibitory effect of compounds of the compounds of this invention on in vitro TNF production by human monocytes The inhibitory effect of compounds of Formula (I) or (II) on in vitro TNF production by human monocytes may be determined by the protocol as described in Badger et al., EPO published Application 0 411 754 A2, Feb. 6, 1991, and in Hanna, WO 90/15534, Dec. 27, 1990.

EXAMPLE B

Two models of endotoxic shock have been utilized to determine in vivo TNF activity for the compounds of this invention. The protocol used in these models is described in Badger et al., EPO published Application 0 411 754 A2, Feb. 6, 1991, and in Hanna, WO 90/15534, Dec. 27, 1990.

The compound of Example 1 herein demonstrated a positive in vivo response in reducing serum levels of TNF induced by the injection of endotoxin.

EXAMPLE C

Isolation of PDE Isozymes

The phosphodiesterase inhibitory activity and selectivity of the compounds of this inventions can be determined using a battery of five distinct PDE isozymes. The tissues used as sources of the different isozymes are as follows: 1) PDE Ib, porcine aorta; 2) PDE Ic, guinea-pig heart; 3) PDE III, guinea-pig heart; 4) PDE IV, human monocyte; and 5) PDE V (also called "Ia"), canine trachealis. PDEs Ia, Ib, Ic and HI are partially purified using standard chromatographic techniques [Torphy and Cieslinski, Mol. Pharmacol., 37:206–214, 1990]. PDE IV is purified to kinetic homogencity by the sequential use of anion-exchange followed by heparin-Scpharose chromatography [Torphy et al., J. Biol. Chore., 267:1798–1804, 1992].

Phosphodiesterase activity is assayed as described in the protocol of Torphy and Cieslinski, Mol. Pharmacol., 37:206–214, 1990. Positive $IC_{50}$'s in the nanomolar to μM range for compounds of the workings examples described herein for compounds of this invention have been demonstrated.

EXAMPLE D

The ability of selected PDE IV inhibitors to increase cAMP accumulation in intact tissues is assessed using U-937 cells, a human monocyte cell line that has been shown to contain a large amount of PDE IV. To assess the activity of PDE IV inhibition in intact cells, nondifferentiated U-937 cells (approximately $10^5$ cells/reaction tube) were incubated with various concentrations (0.01–1000 μM) of PDE inhibitors for one minute and 1 μM prostaglandin E2 for an additional four minutes. Five minutes after initiating the reaction, cells were lysed by the addition of 17.5% perchloric acid, the pH was neutralized by the addition of 1M potassium carbonate and cAMP content was assessed by RIA. A general-protocol for this assay is described in Brooker et al., Radioimmunassay of cyclic AMP and cyclic GMP., Adv. Cyclic Nucleotide Res., 10:1–33, 1979. The compounds of the working examples as described herein for compounds of this invention have demonstrated a positive $EC_{50}$s in the gM range in the above assay.

We claim:

1. A compound selected from the group consisting of
   4-cyano-4-(3-cyclopentyloxy-4-methoxyphenyl)cyclohex-1-en-1-yl trifluoromethylsulfonate;
   4-cyano-4-(3-cyclopentyloxy-4-methoxyphenyl)-1-methoxycyclohex-1-ene; and
   4-cyano-4-(3-cyclopropylmethoxy-4-methoxyphenyl)cyclohex-1-en-1-yl trifluoromethylsulfonate.

2. A pharmaceutical composition comprising a compound of claim 1 and a pharmaceutically acceptable excipient.

3. A method for treating an allergic or inflammatory disease which method comprises administering to a subject in need thereof an effective amount of a compound of claim 1 alone or in combination with a pharmaceutically acceptable excipient.

4. A compound selected from the group consisting of
   2-carbomethoxy-4-cyano-4-(3-cyclopropylmethoxy-4-methoxyphenyl)-1-(methoxymethyloxy) cyclohex-1-ene;
   2-carboxy-4-cyano-4-(3-cyclopropylmethoxy-4-methoxyphenyl)-1-(methoxymethyloxy) cyclohex-1-ene;
   2-aminocarbonyl-4-cyano-4-(3-cyclopropylmethoxy-4-methoxyphenyl)-1-(methoxymethyloxy) cyclohex-1-ene;
   1-amino-4-(3-cyclopropylmethoxy-4-difluoromethoxyphenyl])-2,4-dicyanocyclohex-1-ene;
   2-carbomethoxy-4-cyano-4-(3-cyclopropylmethoxy-4-difluoromethoxyphenyl)-1-(methoxymethylox) cyclohex-1-ene;
   2-carboxy-4-cyano-4-(3-cyclopropylmethoxy-4-difluoromethoxyphenyl)-1-(methoxymethyloxy) cyclohex-1-ene;
   2-aminocarbonyl-4-cyano-4-(3-cyclopropylmethoxy-4-difluoromethoxyphenyl)-1-(methoxymethyloxy) cyclohex-1-ene;
   1-amino-2-carbomethoxy-4-cyano-4-(3-cyclopentyloxy-4-methoxyphenyl)cyclohex-1-ene;
   methyl 2-5-cyano-5-(R and S)-(3-cyclopentyloxy-4-difluoromethoxyphenyl) cyclohex-1-en-1-yl carboxylate;
   methyl 2-amino-5-cyano-5-(3-cyclopropylmethoxy-4-difluoromethoxyphenyl)-cyclohex -1-en-1-yl carboxylate;
   methyl 2-benzylamino-5-cyano-5-( 3-cyclopropylmethoxy-4-methoxyphenyl)cyclohex-1-en-1-yl carboxylate; or
   methyl 2-5-cyano-5-(R and S)-(3-cyclopentyloxy-4-difluoromethoxyphenyl) cyclohex-1-en-1-yl carboxylate.

5. A pharmaceutical composition comprising a compound of claim 4, and a pharmaceutically acceptable excipient.

6. A method for treating an allergic or inflammatory disease which method comprises administering to a subject in need thereof an effective amount of a compound of claim 4 alone or in combination with a Pharmaceutically acceptable excipient.

* * * * *